(12) United States Patent
Seitz, III

(10) Patent No.: US 11,517,387 B2
(45) Date of Patent: Dec. 6, 2022

(54) MULTIFUNCTIONAL ENCLOSURE FOR MEDICAL PROBES

(71) Applicant: John R Seitz, IV, Oxford, PA (US)

(72) Inventor: John Russell Seitz, III, Lincoln University, PA (US)

(*) Notice: Subject to any disclaimer, the term of this patent is extended or adjusted under 35 U.S.C. 154(b) by 0 days.

(21) Appl. No.: 17/479,559

(22) Filed: Sep. 20, 2021

(65) Prior Publication Data

US 2022/0000574 A1 Jan. 6, 2022

Related U.S. Application Data

(63) Continuation of application No. 16/353,889, filed on Mar. 14, 2019, now Pat. No. 11,123,147, which is a continuation-in-part of application No. 14/936,336, filed on Nov. 9, 2015, now abandoned, which is a continuation of application No. 13/235,522, filed on Sep. 19, 2011, now Pat. No. 9,277,966.

(Continued)

(51) Int. Cl.

| *A61B 90/70* | (2016.01) |
| *A61B 50/20* | (2016.01) |
| *A61B 50/30* | (2016.01) |
| *A61M 25/00* | (2006.01) |
| *A61B 1/00* | (2006.01) |
| *A61B 50/22* | (2016.01) |
| *A61B 1/12* | (2006.01) |

(52) U.S. Cl.
CPC ............ *A61B 50/20* (2016.02); *A61B 1/0014* (2013.01); *A61B 1/00137* (2013.01); *A61B 1/00144* (2013.01); *A61B 1/121* (2013.01); *A61B 50/22* (2016.02); *A61B 50/30* (2016.02); *A61M 25/002* (2013.01); *A61B 2050/314* (2016.02); *A61B 2090/701* (2016.02)

(58) Field of Classification Search
CPC ......... A61B 50/20; A61B 50/22; A61B 50/30; A61B 1/00137; A61B 1/0014; A61B 1/00144; A61B 1/121; A61B 2050/314; A61B 2090/701; A61B 90/70; A61M 25/002

See application file for complete search history.

(56) References Cited

U.S. PATENT DOCUMENTS

| 2,340,024 A | 1/1944 | Skaller |
| 3,203,545 A | 8/1965 | Grossman |

(Continued)

FOREIGN PATENT DOCUMENTS

WO  WO 2008-119118 A1  10/2008

*Primary Examiner* — Jacob K Ackun
(74) *Attorney, Agent, or Firm* — Devlin Law Firm LLC; James M. Lennon

(57) ABSTRACT

A multifunctional enclosure is described having an elongated sleeve configured with an enlarged opening for the insertion of an elongated member of a medical probe. The multifunctional enclosure is configured to prevent the elongated member of the medical probe from swinging and becoming damaged during transport. The multifunctional enclosure may further comprise an attachment component for securing the medical probe to the multifunctional enclosure. Furthermore, at least one vent may be configured onto the multifunctional enclosure, such as on a first end closure portion. The vent may allow for adequate flow for sterilization and/or drying.

19 Claims, 12 Drawing Sheets

Related U.S. Application Data

(60) Provisional application No. 61/386,035, filed on Sep. 24, 2010.

(56) References Cited

U.S. PATENT DOCUMENTS

| | | | |
|---|---|---|---|
| 3,794,042 A | 2/1974 | De Klotz et al. |
| 3,861,395 A | 1/1975 | Taniguchi |
| 3,956,011 A | 5/1976 | Carleton |
| 4,754,877 A | 7/1988 | Johansson et al. |
| 4,772,275 A | 9/1988 | Erlich |
| 4,815,470 A | 3/1989 | Curtis et al. |
| 4,823,949 A | 4/1989 | Bala |
| 4,878,762 A | 11/1989 | Uddo Jr. et al. |
| 4,898,586 A | 2/1990 | McDonough |
| 4,928,917 A | 5/1990 | Wolf |
| 4,997,084 A | 3/1991 | Opie et al. |
| 5,125,416 A | 6/1992 | Phillips |
| 5,217,114 A | 6/1993 | Gadberry et al. |
| 5,340,550 A | 8/1994 | Johnsen et al. |
| 5,415,287 A | 5/1995 | Hamano et al. |
| 5,514,074 A | 5/1996 | Yabe et al. |
| 6,361,751 B1 | 3/2002 | Hight, III |
| 6,375,006 B1 | 4/2002 | Samuels |
| 6,793,882 B1 | 9/2004 | Verschuur |
| 6,994,823 B2 | 2/2006 | Hight, III |
| 7,290,926 B2 | 11/2007 | Yu |
| 7,845,850 B2 | 12/2010 | Hsieh |
| 7,874,426 B2 | 1/2011 | Castellani |
| 9,277,966 B2 | 3/2016 | Seitz, III |
| 11,123,147 B2 * | 9/2021 | Seitz, III ............. A61M 25/002 |
| 2002/0068028 A1 | 6/2002 | Hight, III |
| 2002/0117412 A1 | 8/2002 | Rabiner et al. |
| 2003/0192799 A1 | 10/2003 | Addy et al. |
| 2004/0245136 A1 | 12/2004 | Nordquist |
| 2004/0256264 A1 | 12/2004 | Israelsson et al. |
| 2006/0116551 A1 | 6/2006 | Lovett et al. |
| 2006/0278546 A1 | 12/2006 | State et al. |
| 2007/0009376 A1 | 1/2007 | Hamada et al. |
| 2008/0251102 A1 * | 10/2008 | Haack .................... B08B 1/006 15/104.93 |
| 2008/0271270 A1 * | 11/2008 | Sawada ................. A61B 90/70 15/1 |
| 2008/0319423 A1 | 12/2008 | Tanghoj et al. |
| 2009/0000970 A1 | 1/2009 | Bordeau et al. |
| 2009/0008279 A1 | 1/2009 | Tanghoej |
| 2009/0112063 A1 | 4/2009 | Bakos et al. |
| 2009/0166306 A1 | 7/2009 | Ahearn |
| 2009/0200187 A1 | 8/2009 | Nestenborg et al. |
| 2010/0042045 A1 | 2/2010 | Splvey |
| 2010/0087801 A1 | 4/2010 | Torstensen et al. |
| 2011/0137428 A1 | 6/2011 | Terliuc |
| 2015/0090620 A1 | 4/2015 | Seitz, III |

* cited by examiner

MULTIFUNCTIONAL ENCLOSURE FOR MEDICAL PROBES

CROSS-REFERENCE TO RELATED APPLICATIONS

This application is a continuation of U.S. patent application Ser. No. 16/353,889, filed Mar. 14, 2019, now issued as U.S. Pat. No. 11,123,147, which is a continuation in part of U.S. patent application Ser. No. 14/936,336, filed Nov. 9, 2015, now abandoned, which is a continuation of U.S. patent application Ser. No. 13/235,522, filed Sep. 19, 2011, and now issued as U.S. Pat. No. 9,277,966, which claims the benefit of priority to U.S. Provisional Patent Application No. 61/386,035, filed Sep. 24, 2010, the disclosures of which are incorporated herein in their entirety.

BACKGROUND OF THE INVENTION

Field of the Invention

The invention relates to multifunctional enclosures for medical probes including endoscopes or instruments and methods of using the enclosure including but not limited to: protecting the medical probe during transport, storing and cleaning the medical probe, enclosing and protecting the medical probe during sterilization, and providing a post procedural reservoir for cleaning and/or sterilizing fluid.

Background

Medical probes are routinely used for various medical procedures whereby they are inserted into the body and in many cases are equipped with a means to view inside the body. Medical probes are expensive instruments that typically comprise an elongated member that is inserted into the body. These elongated members are usually designed to be flexible to allow for maneuvering and locating the tip at a desired location in the body. The flexibility and length of the elongated members of the medical probe make them difficult to handle. The elongated portions of the medical probe may unintentionally swing and hit object during handling or transport and become damaged or contaminated. Medical probes must be sterilized or disinfected after each use, which requires a considerable amount of handling including transport to a cleaning facility, transport to and handling during sterilization/disinfection, transport to and handling during storage, and finally transport to and handling during medical procedures. After a medical procedure is complete, the contaminated medical probe may pose a contamination risk to the operating room, or other medical room. Body fluids and other body contaminates may drip or fling off of the elongated member of the medical probe, and create a cross contamination risk.

During sterilization/disinfection procedures, the medical probe, or in some cases the elongated member of the medical probe, may be placed into a sterilization/disinfection chamber, such as, steam, ethylene oxide, ozone or the like. Handling of the medical probe during these repetitive procedures introduces possible cross contamination by placing the device directly on surfaces where other devices have previously been located. In addition, these repetitive procedures subject the medical probe to damage, along the length, and especially to the highly sensitive tip of the medical probe.

There exists a need for a multifunctional enclosure for medical probes that can be used to protect the elongated member of the medical probe during transport, storage, cleaning, sterilization, and provide a post procedural reservoir for cleaning and/or sterilizing fluid.

SUMMARY OF THE INVENTION

The invention is directed to a multifunctional enclosure for medical probes and in particular the elongated members of an endoscopic device. The multifunctional enclosure comprises an elongated sleeve having a first end, a second end and an attachment component. The first end may be closed and the elongated member of the medical probe may be inserted through the second end. The elongated sleeve may be rigid in order to prevent the elongated member of the medical probe from swinging or moving during transport or handling. In one embodiment, the elongated sleeve is a tube, and may be a plastic tube. The elongated sleeve may be configured in a generally straight shape, or comprise at least one bend or curve. In addition, the elongated sleeve as described herein, may be a "U" shape, or configured in a helical shape, wherein at least a portion of the elongated sleeve is in a helical configuration. The elongated sleeve may have an aspect ratio of greater than about 3, or more.

The first end of the multifunctional enclosure may be closed or may comprise a detachable first end cover portion, such as a cap or plug. The first end cover portion may be removed during cleaning or sterilization procedures to allow for flow through the elongated sleeve. In addition, the first end cover portion may be removed to allow for adequate drying after cleaning or sterilization. In one embodiment the first end, or first end cover portion comprises a vent. A vent may be configured anywhere on the multifunctional enclosure, and the vent may be an antimicrobial, and/or hydrophobic. In yet another embodiment the first end cover portion comprises a seam where the first end of the multifunctional enclosure has been sealed. For example, the first end of a plastic multifunctional enclosure may be heat pressed and welded together for form a seal. In still another embodiment, the first end of the multifunctional enclosure may be molded in such a way to form a cover over the end of the elongated member of the multifunctional enclosure.

A pouch, cap or plug may be attached or sealed over the first end or second end to protect interior of the multifunctional enclosure from contaminates prior to use. The pouch, cap or plug may be removed prior to use and a clean first end cover portion may be used attached to the first end.

The second end of the multifunctional enclosure may comprise an enlarged end or opening configured to facilitate the insertion of the medical probe. The second end may be a funnel shape or an irregular shape. In one embodiment, the second end comprises a cover that may be removed to allow for the insertion of the medical probe. In an alternative embodiment, the second end cover may comprise an opening, such as a hole or at least one slit, whereby the medical probe may be inserted. The second end cover may protect the interior of the multifunctional enclosure from contamination prior to use. In one embodiment the multifunctional enclosure, comprises two second end covers; one being solid, and the other having an opening. In this embodiment, the solid second end cover may be removed and the medical probe may be inserted through the opening in the other second end cover. The second end may further comprise at least one flute whereby the air may pass when a medical probe is inserted into the multifunctional enclosure. The flute or flutes may comprise channels along at least a portion of the length of the enlarged end. In one embodiment, the second end comprises a plurality of flutes extending the length of the enlarged end.

The attachment component may comprise any number of components configured to attach the multifunctional enclosure to the medical probe. The attachment component may include for example, elastic bands, hooks, latches, hook and loop fasteners and the like. In one embodiment, the attachment component comprises at least one elastic band that may be detachably attached to the medical probe, such as by stretching the band and locating the stretched end over a portion of the medical probe.

The multifunctional enclosure may further comprise an enclosure pouch that may be configured to enclose the end of the medical probe that extends from the multifunctional enclosure. In one embodiment, the enclosure pouch is attached to the multifunctional enclosure, and comprises a sealing portion along the extended end that may be used to seal the medical probe within the enclosure pouch.

The multifunctional enclosure as described herein may be used in a variety of ways. In one method of use, a medical probe or the elongated member of a medical probe may be inserted into the multifunctional enclosure as described herein, and the medical probe may be securely transported to and/or from, a medical procedural room, storage area, cleaning facility, or a sterilization procedure. In another embodiment, the multifunctional enclosure may be used as a reservoir for fluids that may coated onto the medical probe prior or after a procedure. For example, the medical probe may be coated with a sterilization fluid prior to a procedure by introducing the fluid into the multifunctional enclosure. The medical probe may then be removed from the multifunctional enclosure and inserted into a patient. In addition, the medical probe may be coated or treated with a cleaning solution or sterilization fluid after a procedure. For example a cleaning fluid, such as enzyme soap, for example, may be introduced into the multifunctional enclosure, and the medical probe may be inserted into the multifunctional enclosure for post procedural cleaning. Quickly treating the medical probe with a cleaning or sterilization fluid after a procedure may reduce the risk of cross contamination occurring and may provide for more effective and complete removal of biological material.

The summary of the invention is provided as a general introduction to some of the embodiments of the invention, and is not intended to be limiting. Additional example embodiments including variations and alternative configurations of the invention are provided herein.

BRIEF DESCRIPTION OF THE DRAWINGS

The accompanying drawings are included to provide a further understanding of the invention and are incorporated in and constitute a part of this specification, illustrate embodiments of the invention, and together with the description serve to explain the principles of the invention.

Detailed Description of the Illustrated Embodiments

Figure 1:
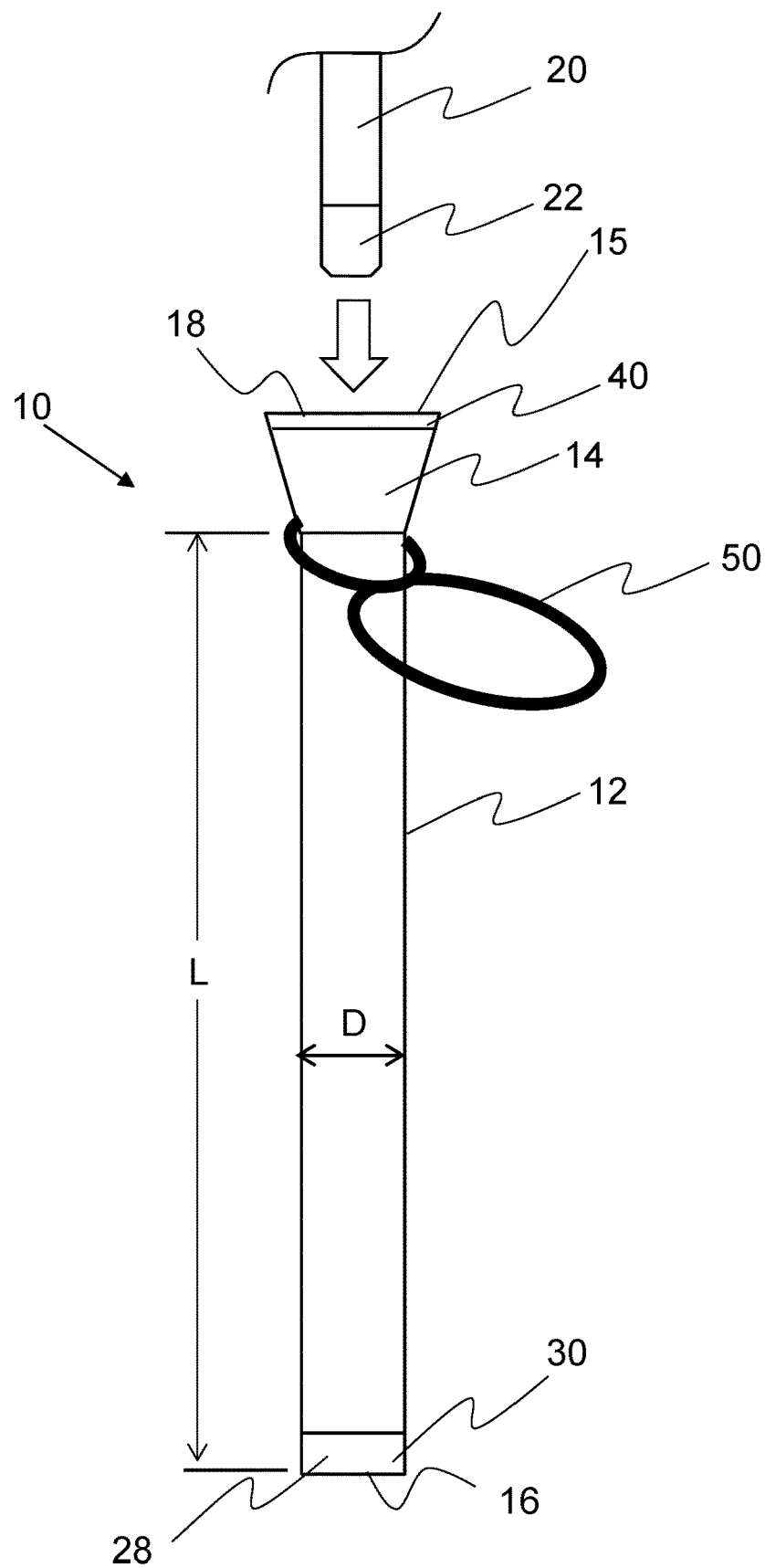
Figure 2A:
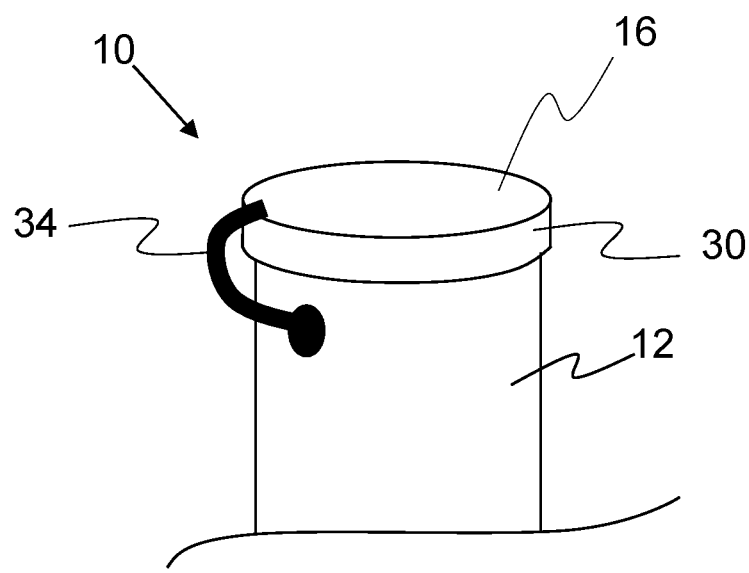
Figure 2B:
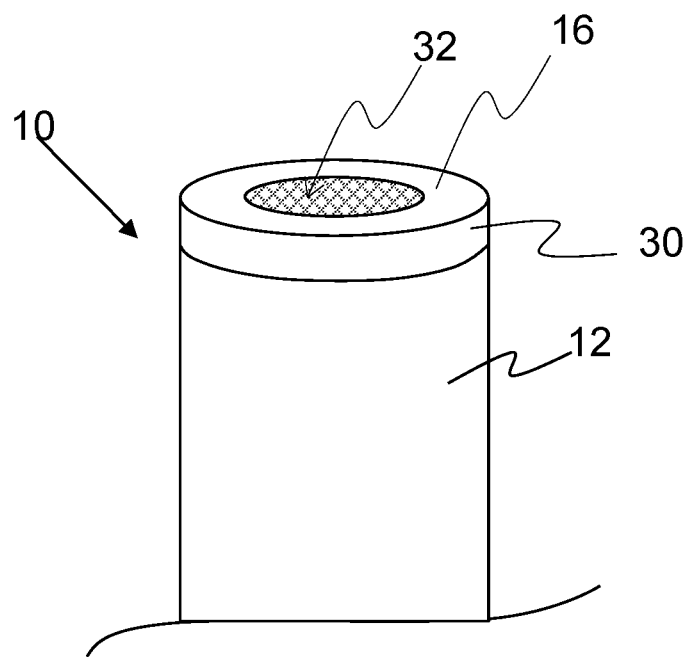
Figure 2C:
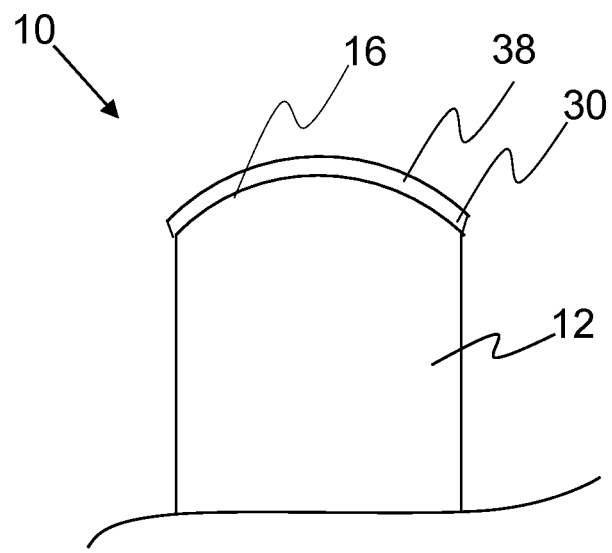
Figure 2D:
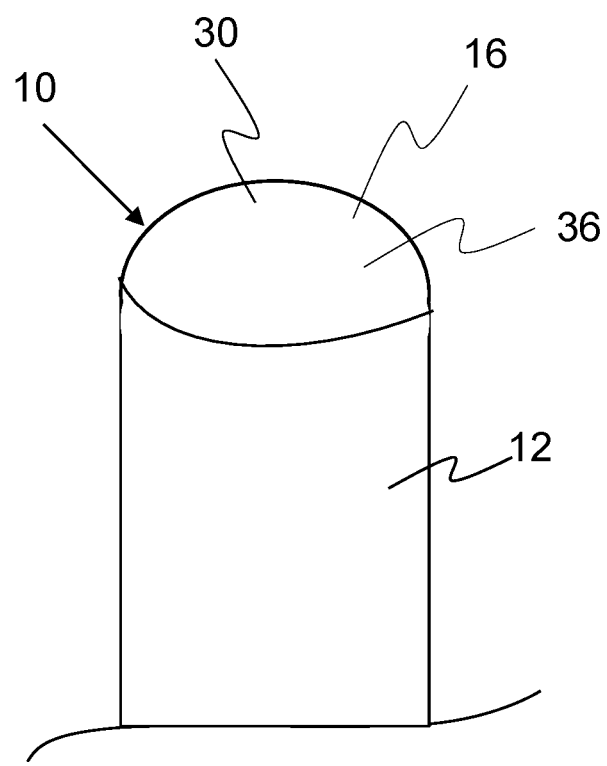
Figure 3A:
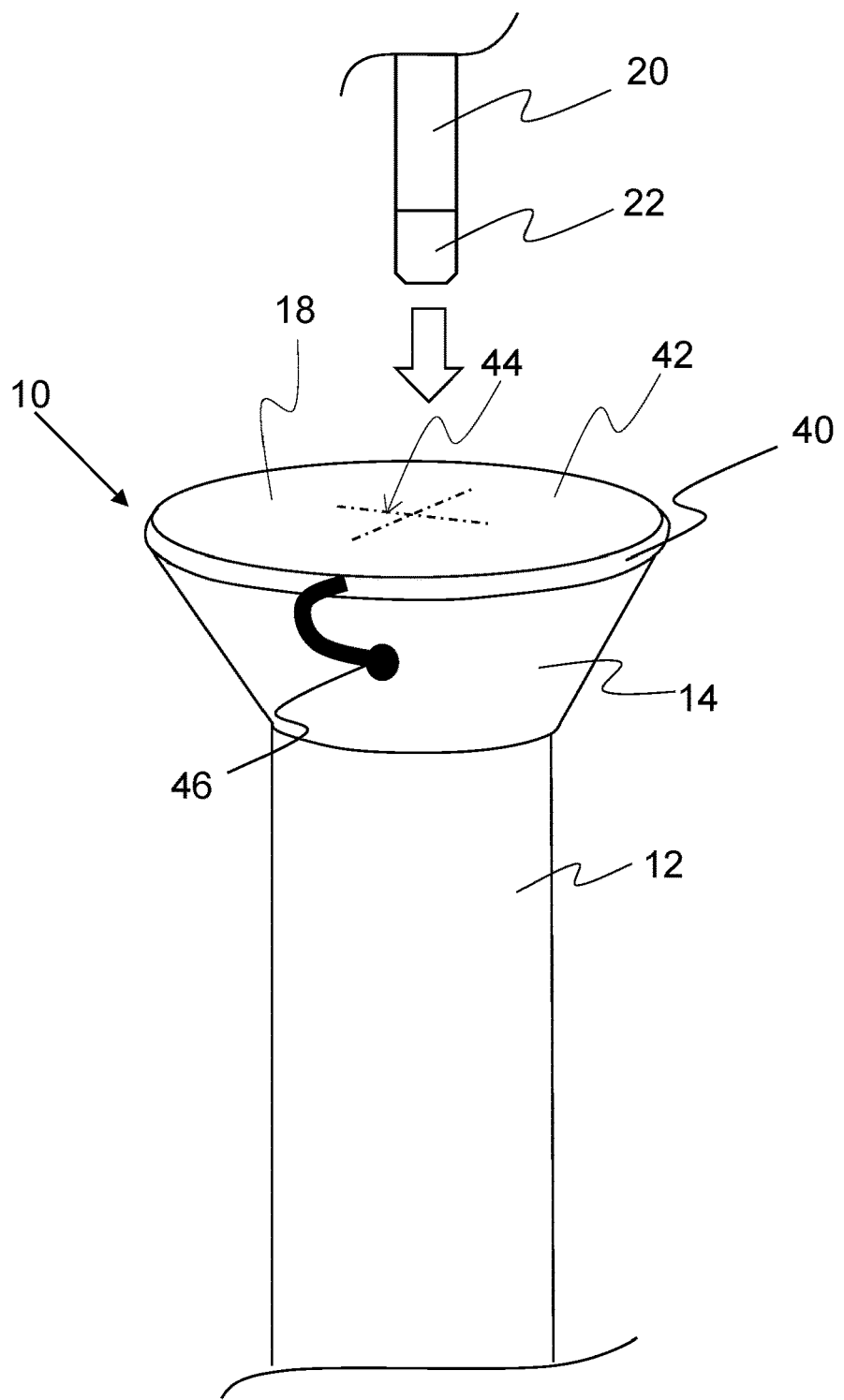
Figure 3B:
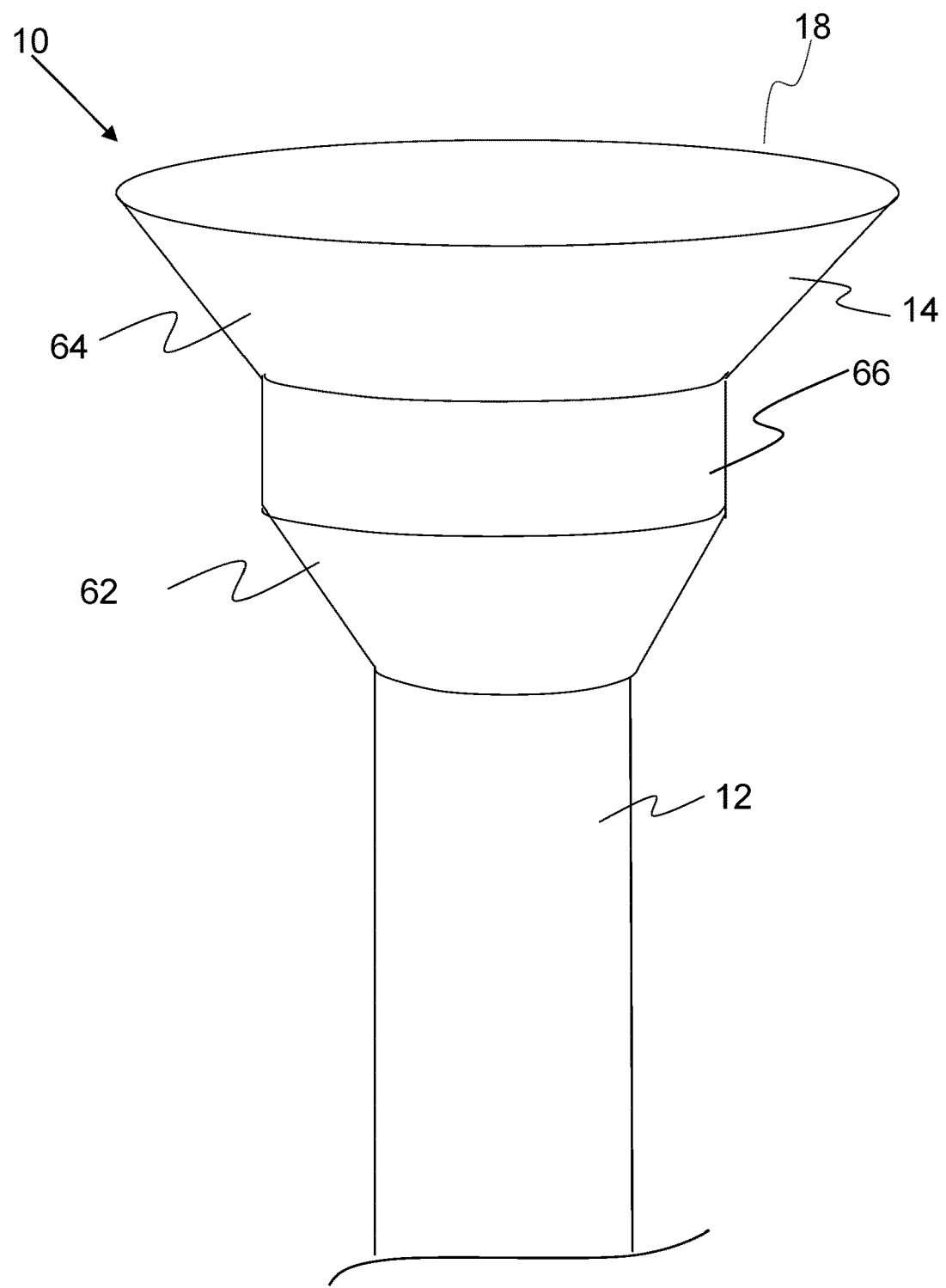
Figure 3C:
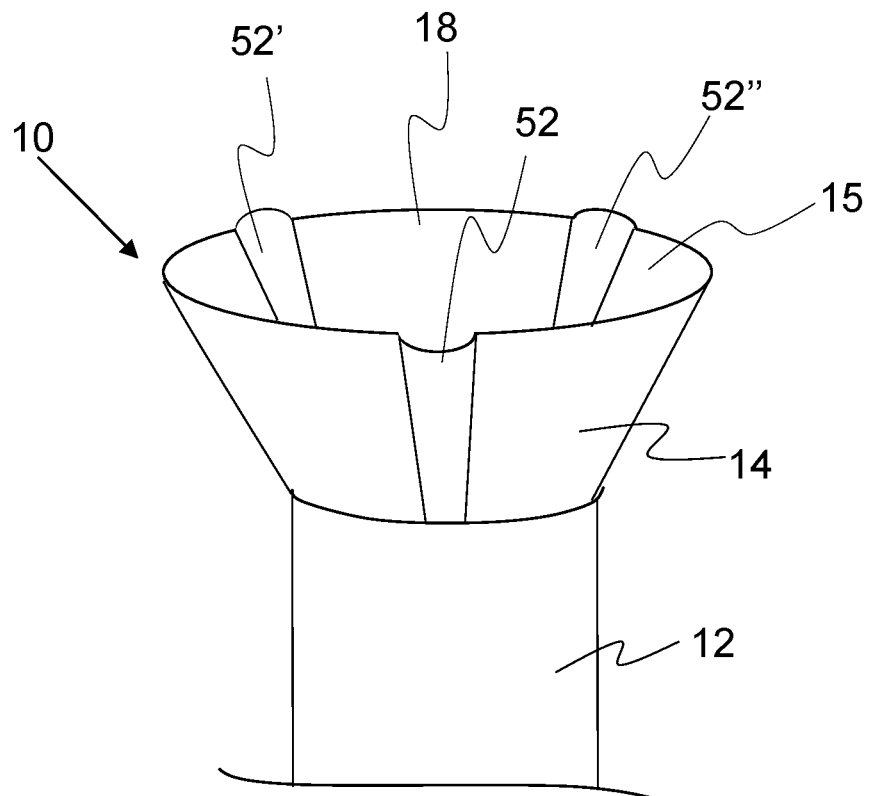
Figure 3D:
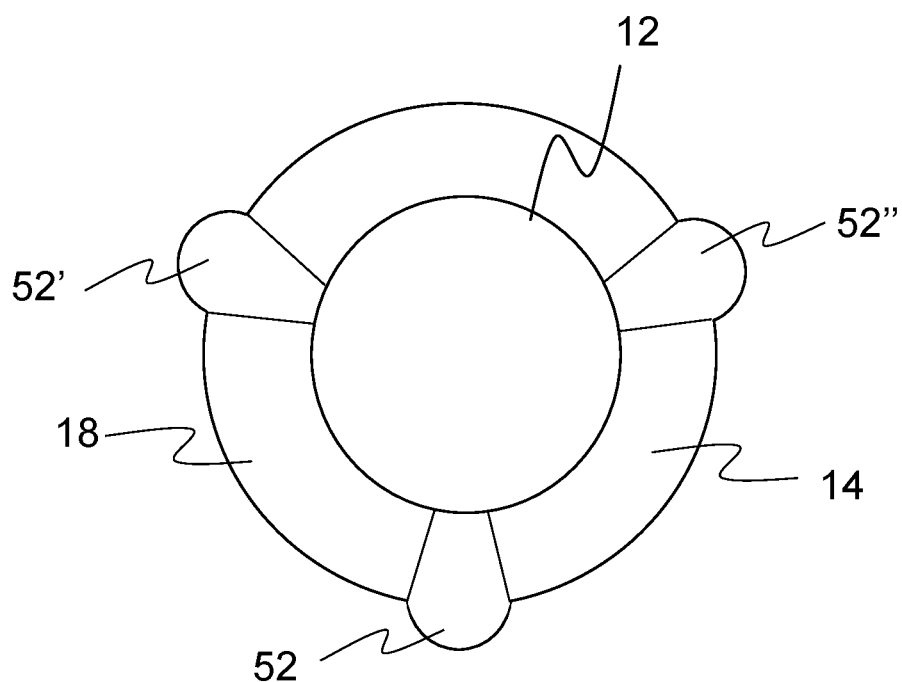
Figure 4:
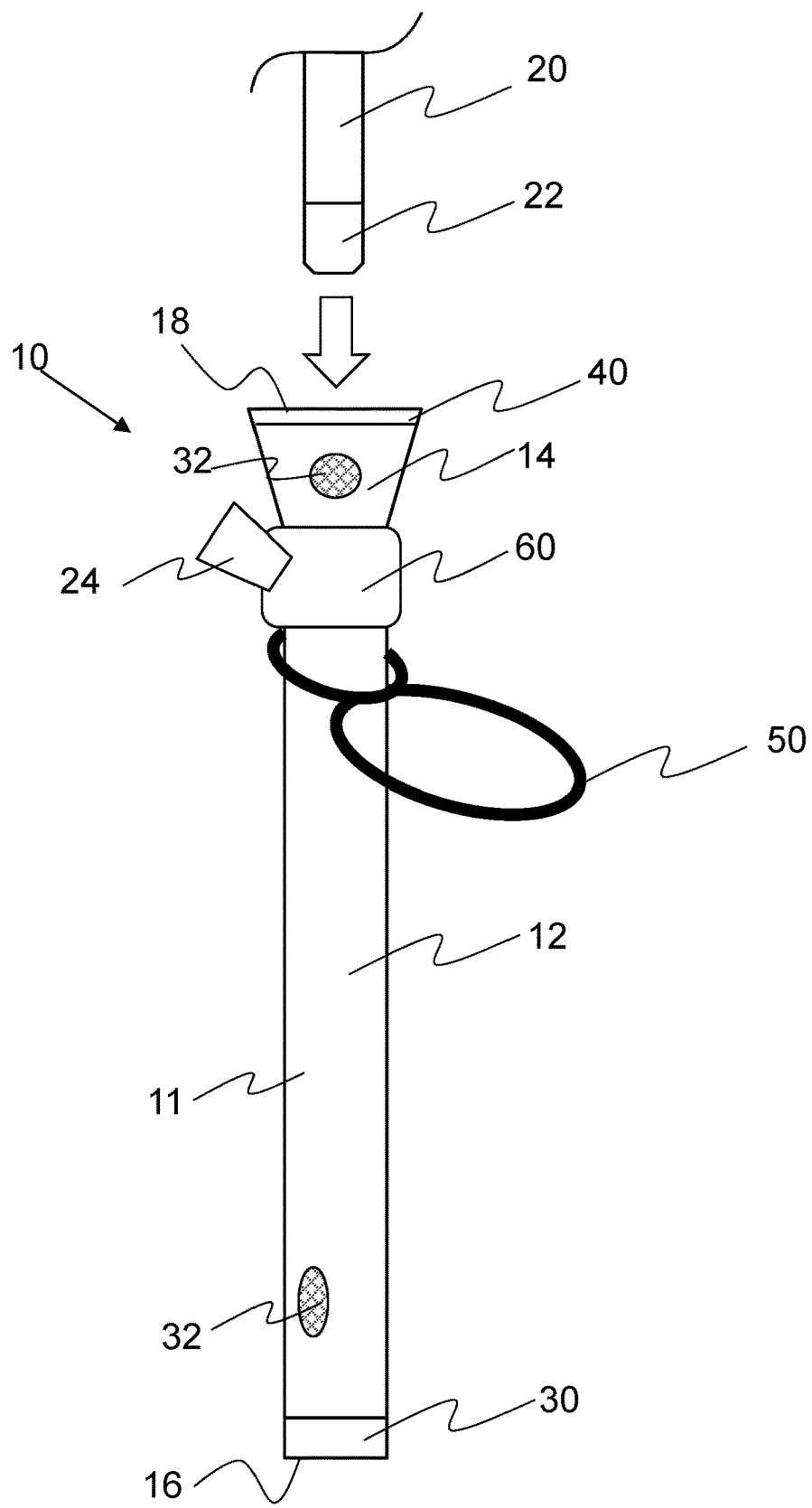
Figure 5A:
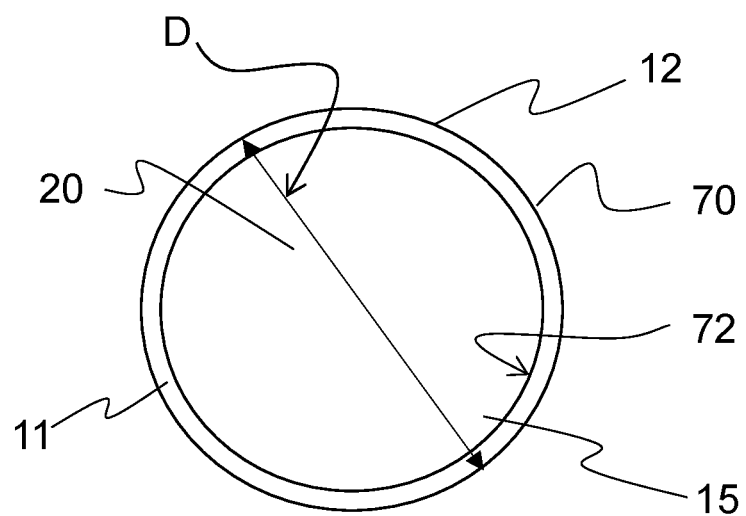
Figure 5B:
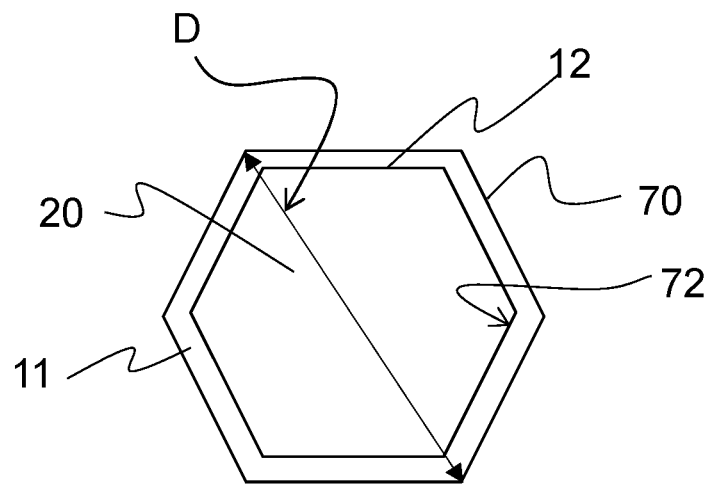
Figure 6A:
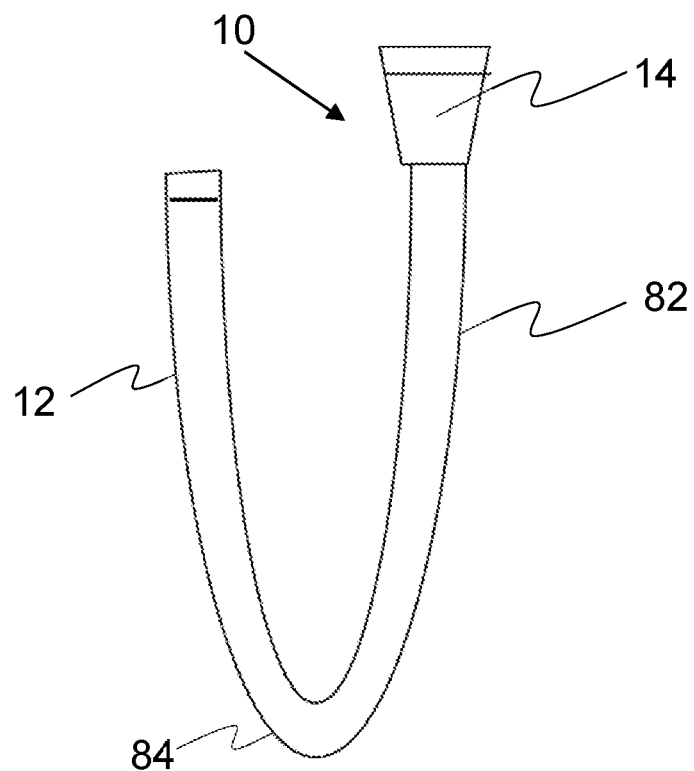
Figure 6B:
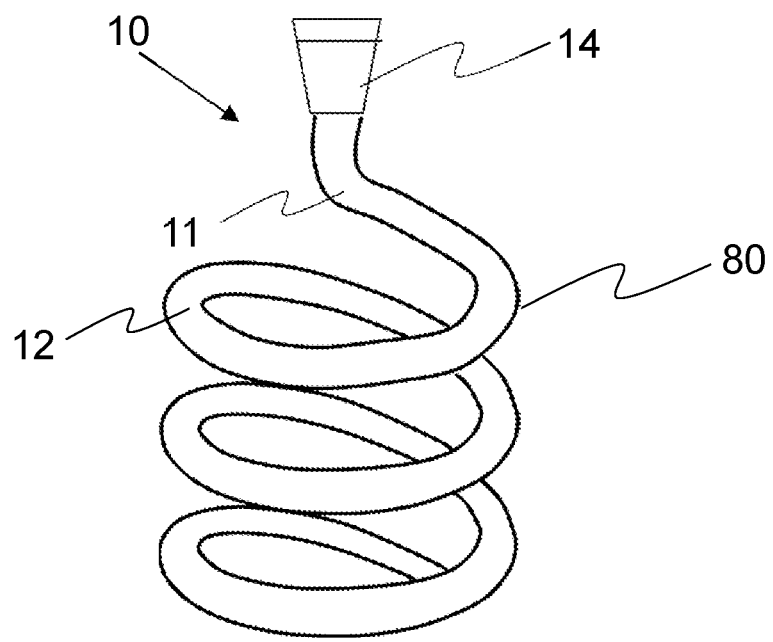
Figure 7:
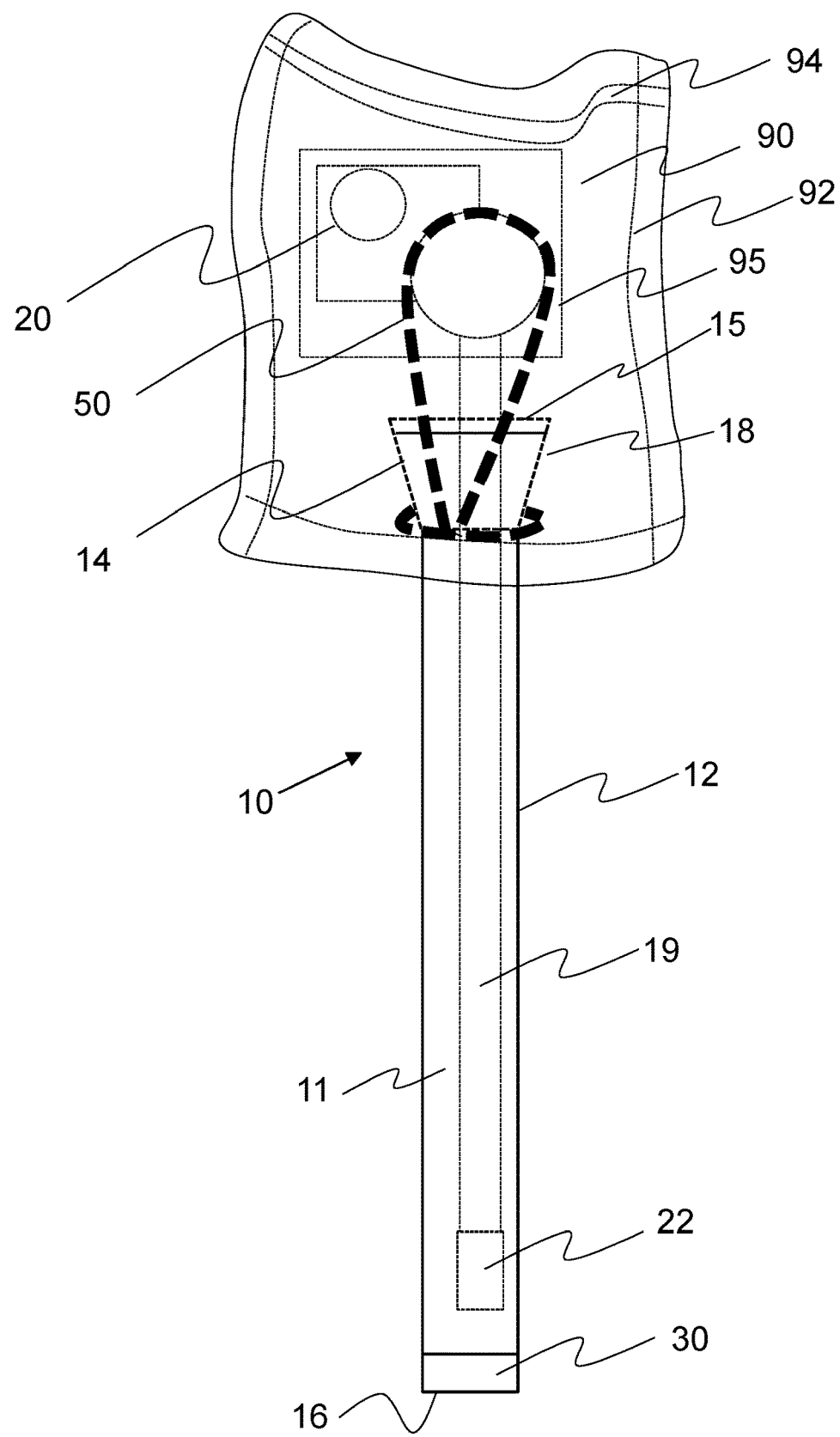
Figure 8A:
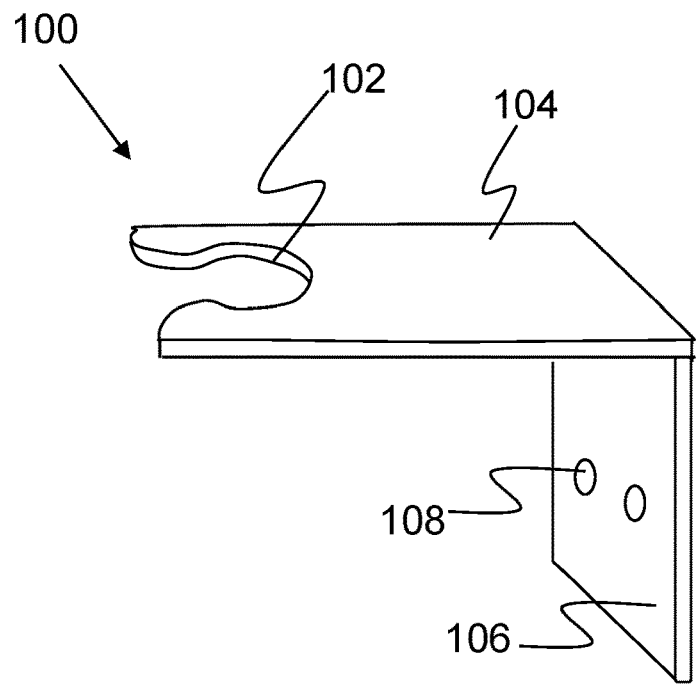
Figure 8B:
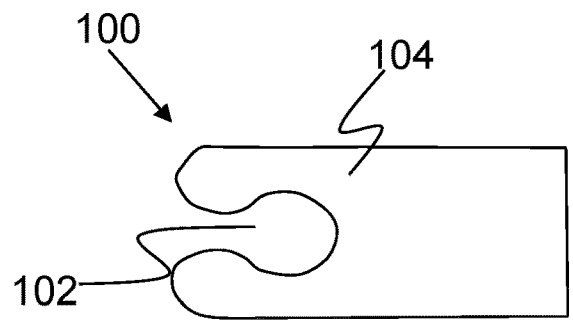
Figure 8C:
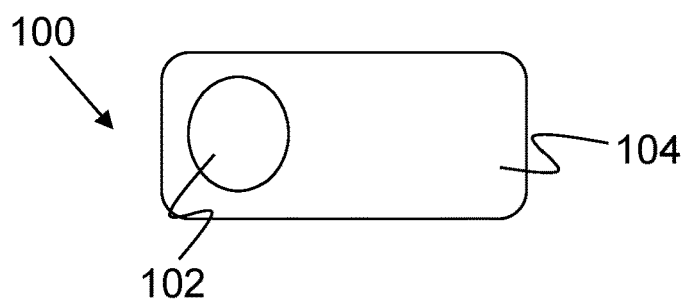
Figure 9:
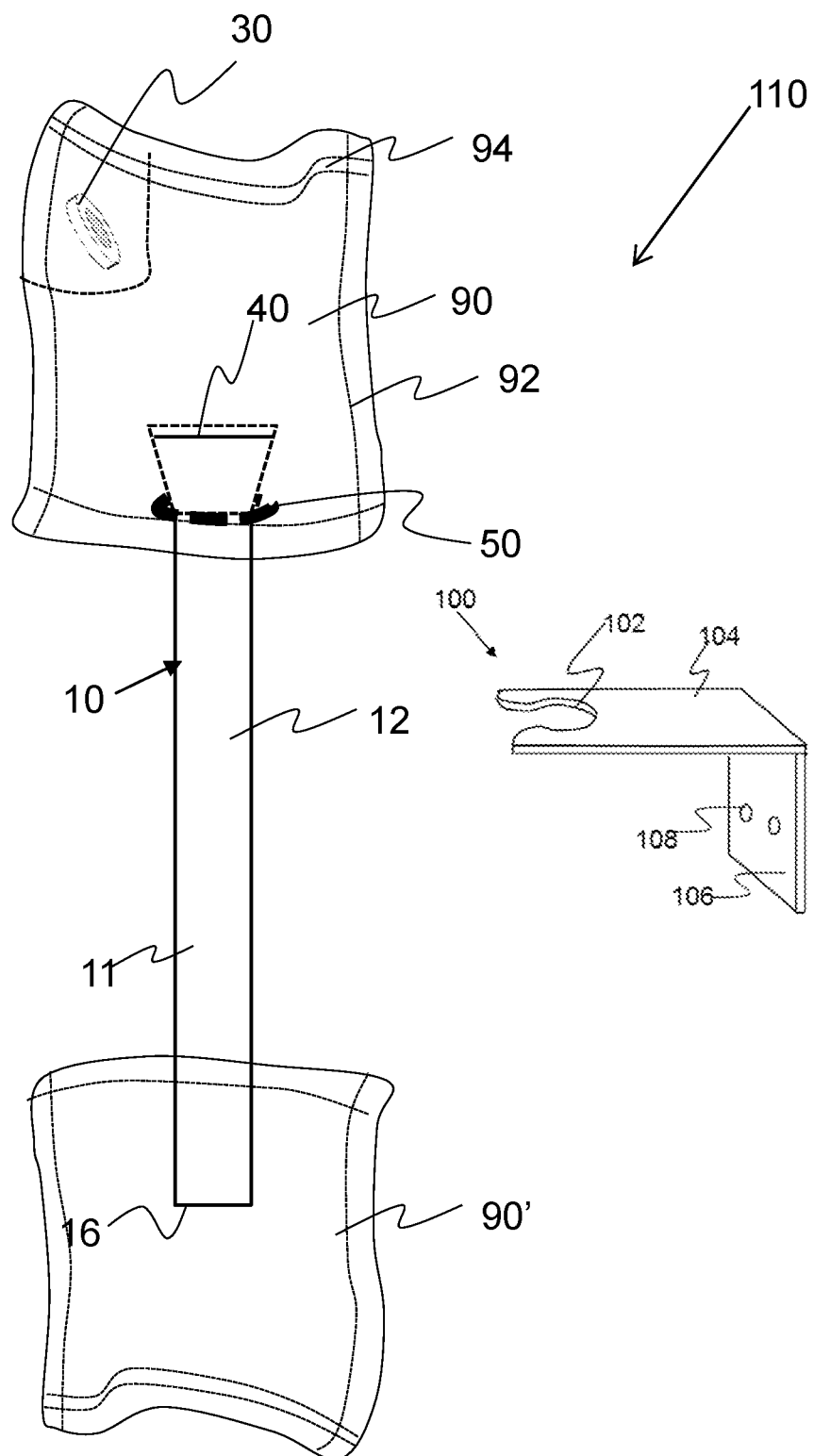

FIG. 1 shows a side view of a multifunctional enclosure described herein.
FIG. 2A shows an isometric view of the first end of a multifunctional enclosure described herein.
FIG. 2B shows an isometric view of the first end of a multifunctional enclosure described herein having a vent.
FIG. 2C shows a side view of the first end of a multifunctional enclosure described herein having a seam.
FIG. 2D shows an isometric view of the first end of a multifunctional enclosure described herein having molded end.
FIG. 3A shows an isometric view of the second end of a multifunctional enclosure described herein having a second end cover.
FIG. 3B shows an isometric view of the second end of a multifunctional enclosure described herein.
FIG. 3C shows an isometric view of the second end of a multifunctional enclosure described herein having flutes.
FIG. 3D shows a top down view of the second end of a multifunctional enclosure described herein having flutes,
FIG. 4 shows a side view of a multifunctional enclosure described herein having an attachment component and two vents.
FIG. 5A show a cross sectional view of the elongated sleeve described herein.
FIG. 5B show a cross sectional views of the elongated sleeve described herein.
FIG. 6A shows a side view of a multifunctional enclosure described herein having a "U" shaped elongated sleeve.
FIG. 6B shows a side view of a multifunctional enclosure described herein having a helically shaped elongated sleeve.
FIG. 7 shows a side view of a multifunctional enclosure described herein having an enclosure pouch.
FIG. 8A shows an isometric view of a bracket described herein.
FIG. 8B and 8C show top views of brackets described herein.
FIG. 9 shows an isometric view of a multifunctional enclosure kit described herein.

Reference numbers to elements are used consistently throughout the figures; however, the elements may have different embodiments such as shape, or configuration, for example.

EXAMPLE EMBODIMENTS

The invention is directed to a multifunctional enclosure for medical probes and in particular the elongated members of a medical probe. As shown in FIG. 1, the multifunctional enclosure 10 comprises an elongated sleeve 12 having a first end 16, a second end 18 and an attachment component 50. In this embodiment, the first end comprises a first end closure portion 30, and the elongated member of the medical probe may be inserted through the second end. The elongated sleeve 12 may be rigid as defined herein, in order to prevent the elongated member of the medical probe from swinging or moving during transport or handling. The elongated sleeve may be made out of any suitable material including but not limited to plastic, metal, glass, composites, combinations of said materials, and the like. The elongated sleeve may be transparent or translucent, opaque or a specific color to indicate a particular type of multifunctional enclosure. In some embodiments, the multifunctional enclosure, or the elongated sleeve of the multifunctional enclosure may be transparent to allow for easy recognition of the medical probe inside. In addition, a transparent or translucent multifunctional enclosure, may allow a user to determine the level of cleaning or other fluid introduced into the multifunctional enclosure.

In one embodiment, the elongated sleeve is a tube, such as a plastic tube. The elongated sleeve may be configured in a generally straight shape, or comprise at least one bend or curve. In addition, the elongated sleeve as described herein may be a "U" shape 82 as shown in FIG. 6A having a bend 84. In another embodiment, the elongated sleeve, or a portion of the elongated sleeve 12 may be configured into helical shape. The helical elongated sleeve 80, may comprise one or more generally straight sections as shown in FIG. 6B.

The elongated sleeve may have an aspect ratio of length L over maximum outer dimension, or outer diameter D, as shown in FIG. 1, greater than about 3, or more. The maximum outer dimension D is the maximum dimension that can be measured across the cross section of the elongated member as shown for example in FIGS. 5A and 5B. When the elongated member is a tube with opening 15, the maximum outer dimension is simply the outer diameter of the tube as shown in FIG. 5A. When the elongated member is a polygonal or irregular shape it is the maximum dimension measured as shown in FIG. 5B. The aspect ratio of the elongated sleeve may be any suitable value such as but not limited to greater than about 5, greater than about 8, or greater than about 10, to accommodate various types of medical probe.

The length of the elongated member of the multifunctional enclosure can be any suitable length to accommodate the medical probe and may be, for example, greater than about 6 in, greater than about 12 in, greater than about 20 in, greater than about 40 in, greater than about 60 in, greater than about 80 in, or any range between lengths described including, for example, from about 6 in to 80 in, or 6 in to 60 in.

The diameter or maximum outer dimension of the elongated member of the multifunctional enclosure may be any suitable dimension to accommodate the medical probe and may be, for example, greater than about 0.1875 in, greater than about 0.25 in, greater than about 0.5 in, greater than about 1.0 in, greater than about 1.25 in, greater than about 1.5 in, greater than about 2.0 in, or any range between lengths described including, for example, from about 0.1875 in to 2.0 in, or 0.25 in to 1.5 in.

The elongated sleeve of the multifunctional enclosure may have any suitable cross sectional shape, such as a circular shape as shown in FIG. 5A, or a polygon shape, as depicted in FIG. 5B as a hexagonal shape. Any suitable shape may be used, and in some embodiments, an irregular or polygonal shape may be used to avoid creating a seal against the medical probe at the second end. The elongated sleeve 12 is configured such that the medical probe 20 may easily slide in and out as shown in FIG. 1. The medical probe may be positioned within the elongated sleeve through the opening 15 with a sufficient clearance from the inside surface 72.

The first end 16 of the multifunctional enclosure 10 may comprise a first end closure portion 30, such as a detachable cap 28, as shown in FIG. 1. The first end closure portion may be removed during cleaning or sterilization procedures to allow for flow through the elongated sleeve. In addition, the first end closure portion may be removed to allow for adequate drying after cleaning or sterilization. A first end closure attachment portion 34, as shown in FIG. 2A, may allow the first end cover to be removed from the end without being completely removed from the multifunctional enclosure. The first end closure attachment portion may comprise any suitable means to attach the first end closure portion 30 to the multifunctional enclosure 10. As shown in FIG. 2A, the first end closure attachment portion 34 comprises a piece of material attached to the first end cover at one end and attached to the elongated member at the opposing end.

The first end closure portion may be a cap that extends over the outer surface of the elongated member, or may be a plug that comprises a portion that is inserted into the opening of the first end. The first end closure portion may be configured to be detachably attached to the first end and may comprise threads such that the first end portion may be screwed onto the first end. Threads may be configured onto the inside and/or outside surface of either the first end closure portion or the first end. In another embodiment, the first end closure portion may be pushed onto the first end and may be designed with tolerances to adequately seal the first end. In addition, the first end closure portion may be snapped onto the first end, and either the closure portion or the first end may comprise at least one raised element, or ridge, that provides an interference fit for the closure portion to be snapped on. In yet another embodiment, the first end closure portion may expand or contract to seal the first end. The first end closure portion may comprise an elastomer to secure the closure portion to the first end.

In yet another embodiment, the first end closure portion comprises a seam 38 where the first end 16 of the multifunctional enclosure 10 has been sealed as shown in FIG. 2C. For example, the first end of a plastic multifunctional enclosure may be heat pressed and welded together to form a seal and first end closure portion. In still another embodiment, the first end 16 of the multifunctional enclosure 10 may comprise a molded end 36, as shown in FIG. 2D. The molded end may be configured in any suitable shape, such as a rounded or spherical shape.

In one embodiment, the first end, or first end cover 30 comprises a vent 32 as shown in FIG. 2B. A vent, however, may be configured anywhere on the multifunctional enclosure 10 as shown in FIG. 4. The vent may be antimicrobial, and/or hydrophobic. In one embodiment, the vent comprises a porous material that meets standards for antibacterial ratings, such as materials having a log reduction value (LRV) of more than 99.999 when tested according to ASTM F1608. The vent may have sufficient air flow to allow for adequate drying of the medical probe after cleaning, sterilization, or during storage. The vent may comprise a material that has a gurley value as measured with a Gurley Densometer 4380, of no more than 100 seconds, and may have gurley values of no more than about 5 seconds, no more than about 20 seconds, no more than about 50 seconds. The vent material may comprise expanded polymers such as expanded polytetrafluoroethylene membrane, microfiber materials, sintered polymers such as Zitex membranes available from Saint Gobain Inc., Worchester, Mass., SureVent membranes available from Millipore Inc., Bellercia, Mass., and the like. The hydrophobic vent may allow fluid to be poured into the enclosure while also allowing for adequate air flow during sterilization and/or drying.

The second end 18 or opening of the multifunctional enclosure 10 may comprise an enlarged end 14, or configured to facilitate the insertion of the medical probe, as shown in FIG. 3A. The second end may be any suitable shape such as a funnel or bell shape. As shown in FIG. 3A the enlarged end 14 is in a funnel shape, where the second end 18 is larger in diameter than the elongated sleeve 12. As shown in FIG. 3B, the enlarged end 14 comprises a plurality of shapes, including a first funnel shape portion 62 and a second funnel shape portion 64. A straight shape portion 66 connects the two funnel shape portions as shown in FIG. 3B.

The enlarged portion 14 may further comprise flutes 52, 52' and 52" as shown in FIG. 3C and 3D. The flutes may be configured into the enlarged portion to allow the passage of air when a medical probe is inserted into the multifunctional enclosure. In some embodiments, the medical probe may fit snugly into the opening 15 at the second end 18 of the multifunctional enclosure and effectively prevent air passage through the second end into the elongated sleeve. The flutes may have any suitable shape such as a curved or angled shape. The flutes may extend the entire length of the enlarged portion, or only a portion of the length of the enlarged portion. In one embodiment, a flute or flutes may extend along a portion of the elongated sleeve.

In one embodiment, the second end comprises a cover 40 that may be removed to allow for the insertion of the medical probe. In an alternative embodiment, the second end cover 40 may comprise an opening 44, such as a hole or at least one slit, whereby the medical probe 20 may be inserted, as shown in FIG. 3A. The second end cover may protect the interior of the multifunctional enclosure from contamination prior to use. In one embodiment, the multifunctional enclosure comprises two second end covers; one being solid, and the other having an opening. In this embodiment, the solid second end cover may be removed and the medical probe may be inserted through the opening in the second end cover. The second end cover may also be attached to the multifunctional enclosure by a second end cover attachment portion 46, as shown in FIG. 3A.

The attachment component 50, as shown in FIG. 1 may comprise any number of components configured to attach the multifunctional enclosure 10 to the medical probe 20. The attachment component may include for example, elastic bands, hooks, latches, hook and loop fasteners and the like. In one embodiment, the attachment component comprises at least one elastic band that may be detachably attached to the medical probe, such as by stretching the band and locating the stretched end over a portion or projection of the medical probe.

FIG. 7 illustrates the multifunction enclosure according to one embodiment of the present invention. It depicts a medical probe 20 for use with the multifunction enclosure 10. The medical probe 20 includes a handle portion 95 and an elongated portion 19. The multifunctional enclosure 10 may further comprise an enclosure pouch 90 that may be configured to enclose the medical probe 20 as shown in FIG. 7. In one embodiment, the enclosure pouch 90 is attached to the multifunctional enclosure 10 and comprises a sealing portion 94 along the extended end that may be used to seal the medical probe 20 within the enclosure pouch as shown in FIG. 7. The elongated portion 19 of the medical probe 20 is inserted through the opening 15 in the second end 18 of the multifunction enclosure 10, and is further restrained by the attachment component 50 that is looped around a portion of the medical probe as shown in FIG. 7. The pouch may comprise any suitable material including but not limited to plastic, metal foil, fabric, antimicrobial materials, such as porous or microporous materials, combinations of material, and the like. The pouch 90 may be a sterilization pouch, and may comprise a porous side and a non-porous side. For example, the pouch may comprise a paper side and a plastic side. The sealing portion of the pouch 94 may comprise any suitable sealing mechanism or material, including but not limited to a zipper, hook and loop fastener, adhesive, interference fit seal, thermally welded seal, and the like. Some special adhesive zones 94 can be configured to aid in sealing around cables and tubing that extend from some styles of endoscopes.

In one embodiment, both the first and second end of the multifunctional enclosure comprise a pouch 90 and 90' that may be removed prior to using the multifunctional enclosure as shown in FIG. 9. The pouches may be attached to one or both ends of the multifunctional enclosure to prevent contamination of the interior 11 of the multifunctional enclosure. The pouches may be attached to the multifunctional enclosure through any suitable means including but not limited to tape, adhesives, heat welding, ultrasonic welding and the like.

The multifunctional enclosure describe herein may be positioned and temporarily restrained by a bracket 100, as shown in FIG. 8A, 8B and 8C. The bracket 100 as shown in FIG. 8A, may have an opening 102 configured in a first member to accept the multifunctional enclosure. The multifunctional enclosure may slide direct into the bracket and the enlarged end of the multifunctional enclosure may support the enclosure. A second member 106 may be attached to the first member 104 of the bracket as shown in FIG. 8A. In addition, the bracket may further comprise at least one attachment portion, such as a hole or holes 108 as shown in FIG. 8A. The opening 102 in the bracket 100 may be configured in any suitable manner to accept and support the multifunctional enclosure as described herein.

The multifunction enclosure as describe herein may be provided as a kit 110 as shown in FIG. 9. The kit 110 may include at least one multifunctional enclosure 10, and a bracket 100. The kit may further include at least one pouch 90 attached to at least one end of the multifunctional enclosure, an attachment component 50, a first end closure portion 30, and a second end cover 40. The first end closure portion 30 may be attached to the first end, or it may be within one of the pouches 90 as shown in FIG. 9.

The multifunctional enclosure as described herein may be used in a variety of ways. In one method of use, a medical probe or the elongated member of a medical probe may be inserted into the multifunctional enclosure as described herein, and the medical probe may be securely transported to and/or from, a medical procedural room, storage area, cleaning facility, repair facility, manufacturer, or a sterilization procedure. In another embodiment, the multifunctional enclosure may be used as a reservoir for fluids that may be coated onto the medical probe prior or after a procedure. For example, the medical probe may be coated with a sterilization fluid prior to a procedure by introducing the fluid into the multifunctional enclosure. The medical probe may then be removed from the multifunctional enclosure and inserted into a patient. The fluid may be simply poured into the second end of the multifunctional enclosure, or a filling port 24, may be configured on the multifunctional enclosure for accepting fluid, as shown in FIG. 4. The filling port may have an adjustable, one way, check valve, or a cover to prevent contaminates from entering the multifunctional enclosure. In addition, the medical probe may be coated or treated with a cleaning solution or sterilization fluid after a procedure. For example, a cleaning fluid such as enzyme soap, for example, may be introduced into the multifunctional enclosure, and the medical probe may be inserted into the multifunctional enclosure for post procedural cleaning. Quickly treating the medical probe with a cleaning or sterilization fluid after a procedure may reduce the risk of cross contamination occurring and may provide for more effective and complete removal of biological material.

The multifunctional enclosure as described herein may be disposable, or may be reusable. A first multifunctional enclosure may be used for sterilization and transport to a medical procedure, and a second multifunctional enclosure may be used for post treatment transport and cleaning.

EXAMPLE

A 30 in long polyethylene terephthalate (PETG) tube having an outer diameter of 0.848 in and a wall thickness of 0.022 in was flared at one end. The flared end, or second end, had a funnel shape and a second end diameter of 1.8 in, and the flared length was approximately 1 in, as measured along the length axis of device. A latex free, synthetic rubber elastic band approximately 3 in in diameter, 0.125 in wide, and 0.0625 in long was configured around the elongated sleeve. A sterilization enclosure pouch available from AMCOR Ltd., having a paper side and a plastic side was attached to the multifunctional enclosure, by a combination of heat sealing and double sided tape.

Definitions

Multifunctional enclosure as used herein is defined as an enclosure that is configured to cover at least the elongated portion of a medical probe and is not configured for insertion into the body.

Medical probe as used herein is defined as any medical device that is inserted into the body for the purpose of imaging, diagnosis and treatment, including but not limited to endoscope, catheter, pressure transducer or ultrasonic imaging device. A medical probe may comprise a flexible or rigid elongated member.

Rigid as used herein in reference to the elongated sleeve portion of the multifunctional enclosure, means that the elongated sleeve will prevent the elongated member of the medical probe from swinging or moving freely. The elongated sleeve may have some flexible properties, such as a plastic tube that may bend to a certain degree under a load, but will permanently deform if bent too far.

Detachably attached as used herein in reference to the first end closure portion means that the first end closure portion can be temporarily attached to the first end of the multifunctional enclosure, such as by screwing, pushing, or snapping on, for example.

As used herein "closure portion," "cover," and "cover portion" are used synonymously to convey a structure that may "close" an opening to limit ingress and egress of fluids or gases to varying degrees.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A multifunctional enclosure system for covering an elongated portion of a medical probe, comprising:
   a) an elongated rigid sleeve comprising:
      i) an interior configured to receive said medical probe;
      ii) a first end;
      iii) a second end comprising an opening, wherein said second end opening is configured for the insertion of said elongated portion of a medical probe; and
      vi) a length extending between said first end and said second end;
   b) a first end closure portion configured on said first end;
   c) a second end cover configured over the second end opening, wherein said interior of said elongated rigid member is protected from contamination prior to use by said second end cover over said second end opening and by said first end closure portion on said first end; and
   d) an attachment component configured to restrain said medical probe to said multifunctional enclosure with said elongated portion of said medical probe configured within said elongated sleeve, and configured to detachably attach to the medical probe;
   wherein said attachment component comprises an elastomeric band configured to attach to the medical probe by stretching over a portion of said medical probe from said multifunctional enclosure.

2. The multifunctional enclosure of claim 1, wherein the attachment component is
   configured as a system of two loops, a first loop and a second loop, wherein said first loop is configured to attach to the exterior of said elongated sleeve, and wherein said second loop is configured to detachably attach to the medical probe by stretching over a portion of said medical probe projecting from said multifunctional enclosure.

3. The multifunctional enclosure of claim 1, wherein the elongated rigid sleeve comprises a plastic tube.

4. The multifunctional enclosure of claim 1, wherein the elongated rigid sleeve is translucent or transparent.

5. The multifunctional enclosure of claim 1, further comprising a vent wherein the elongated sleeve is configured for sterilization, whereby at least one of the second end cover or vent is permeable to allow for the permeation of sterilization gas therethrough.

6. The multifunctional enclosure of claim 1, wherein the elongated rigid sleeve comprises at least one bend.

7. The multifunctional enclosure of claim 1, wherein at least a portion of the elongated rigid sleeve is a helical elongated sleeve.

8. The multifunctional enclosure of claim 1, wherein the second end cover comprises a vent.

9. The multifunctional enclosure of claim 1, wherein the second end further comprises at least one flute.

10. The multifunctional enclosure of claim 1, wherein the second end cover further comprises an enclosure pouch.

11. The multifunctional enclosure of claim 10, wherein the enclosure pouch is configured to extend around a handle portion of the medical probe with the elongated portion of said medical probe configured within said elongated sleeve, wherein the medical probe is configured to be enclosed by the enclosure pouch and the elongated sleeve.

12. The multifunctional enclosure of claim 10, wherein the enclosure pouch comprises a sealing portion configured to seal the enclosure pouch around the elongated sleeve.

13. The multifunctional enclosure of claim 1, further comprising at least one port.

14. The multifunctional enclosure of claim 1, wherein the rigid sleeve has an outer diameter of about 0.8 inches and a wall thickness of about 0.02 inches.

15. The multifunctional enclosure of claim 1, wherein the first end closure portion is configured to be detachably attached to the multifunctional enclosure.

16. The multifunctional enclosure of claim 1, wherein the first end closure portion comprises a seam closure.

17. The multifunctional enclosure of claim 1, wherein the first end closure portion further comprises a vent.

18. The multifunctional enclosure of claim 1, wherein the elongated rigid sleeve has a cross sectional shape selected from the group consisting of: circular, hexagonal, polygonal and irregular.

19. The multifunctional enclosure of claim 1, wherein the second end comprises an enlarged funnel shaped portion.

* * * * *